T866020

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED SEPTEMBER 16, 1969

866 O.G. 702

804,478

METHOD FOR THE PRODUCTION OF ALIPHATIC CONJUGATED DIOLEFINES

Charles R. Noddings, 3610 Boston, Midland, Mich. 48640

Filed Mar. 5, 1969. Published Sept. 16, 1969
Int. Cl. C07c *5/18*
U.S. Cl. 260—680
1 Sheet Drawing. 8 Pages Specification

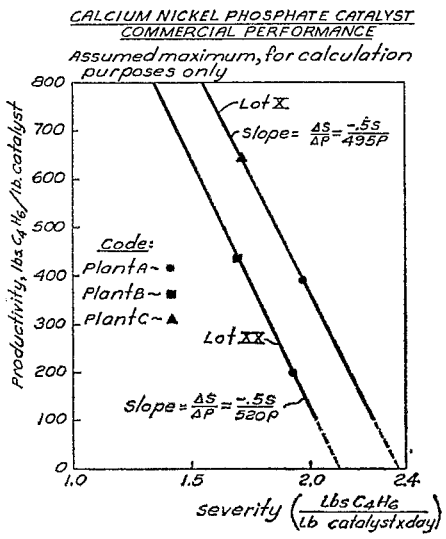

Figure 2:
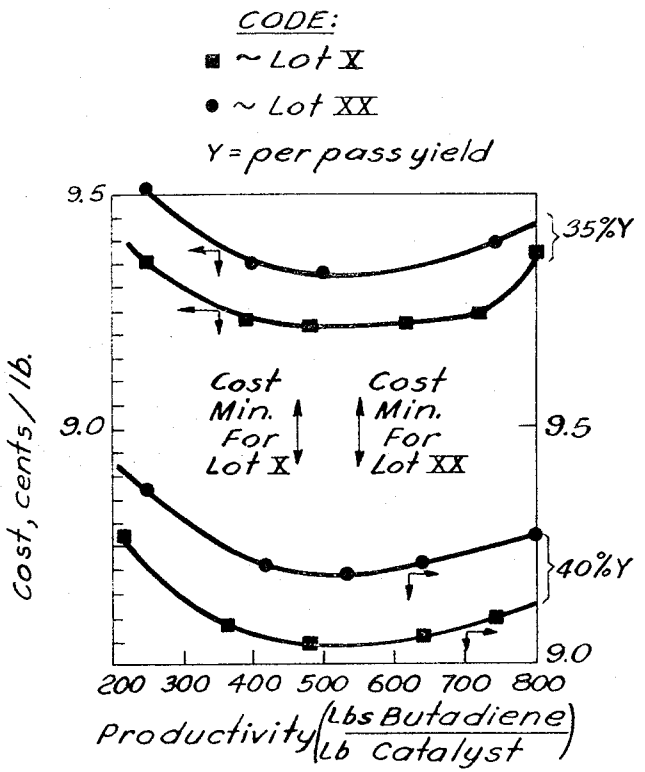
Figure 1:
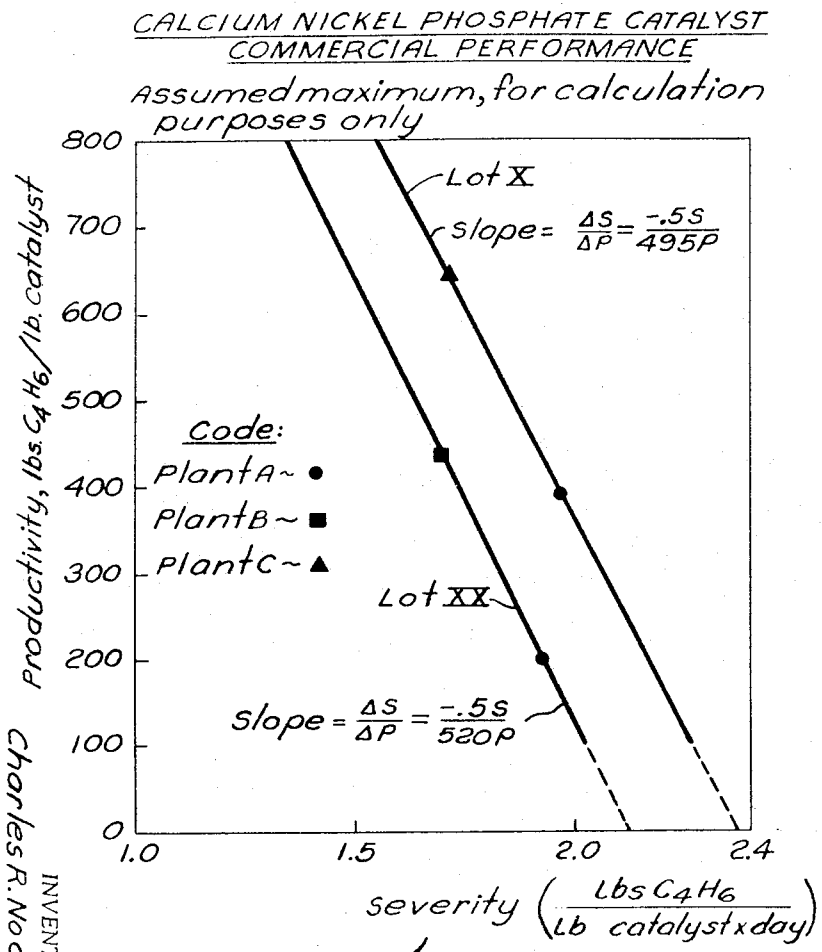

The relationship between severity and total productivity is shown as constant in the production of a diolefin by passing mixtures of steam and an olefin and steam and oxygen through a bed of calcium nickel phosphate catalyst in alternate cycles. FIGURE 1 illustrates this relationship with catalyst lots having different total productivities by showing lines of virtually the same slopes. The severity at which the diolefin should be produced to give a desired productivity may be determined by using to expiration only one batch of catalyst. The productivity which will result in the lowest cost of diolefin may then be selected.

T866020

METHOD FOR THE PRODUCTION OF ALIPHATIC CONJUGATED DIOLEFINES

Filed March 5, 1969

INVENTOR.
Charles R. Noddings

BY

Griswold & Burdick
ATTORNEYS